US010271966B2

(12) United States Patent
Glasgow

(10) Patent No.: US 10,271,966 B2
(45) Date of Patent: Apr. 30, 2019

(54) MECHANICAL PROSTHETIC HAND

(71) Applicant: Ryan William Glasgow, Portland, OR (US)

(72) Inventor: Ryan William Glasgow, Portland, OR (US)

(*) Notice: Subject to any disclaimer, the term of this patent is extended or adjusted under 35 U.S.C. 154(b) by 385 days.

(21) Appl. No.: 15/072,281

(22) Filed: Mar. 16, 2016

(65) Prior Publication Data

US 2017/0266020 A1 Sep. 21, 2017

(51) Int. Cl.
*A61F 2/50* (2006.01)
*A61F 2/58* (2006.01)
*A61F 2/68* (2006.01)
*A61F 2/70* (2006.01)

(52) U.S. Cl.
CPC .............. *A61F 2/583* (2013.01); *A61F 2/586* (2013.01); *A61F 2002/5003* (2013.01); *A61F 2002/5009* (2013.01); *A61F 2002/5073* (2013.01); *A61F 2002/5093* (2013.01); *A61F 2002/587* (2013.01); *A61F 2002/6854* (2013.01); *A61F 2002/701* (2013.01)

(58) Field of Classification Search
CPC .. A61F 2/583; A61F 2/586; A61F 2002/5093; A61F 2002/587
See application file for complete search history.

(56) References Cited

U.S. PATENT DOCUMENTS

| 7,673,916 | B2* | 3/2010 | Greenhill | B25J 15/0009 |
| | | | | 294/106 |
| 9,814,604 | B2* | 11/2017 | Jury | A61F 2/583 |
| 2005/0021155 | A1* | 1/2005 | Brimalm | A61F 2/583 |
| | | | | 623/64 |
| 2012/0186383 | A1* | 7/2012 | Schvalb | A61F 2/586 |
| | | | | 74/490.04 |
| 2013/0331949 | A1* | 12/2013 | Dehoff | A61F 2/583 |
| | | | | 623/26 |
| 2013/0345828 | A1* | 12/2013 | Starkey | A61F 2/586 |
| | | | | 623/64 |
| 2014/0067083 | A1* | 3/2014 | Wenstrand | A61F 2/583 |
| | | | | 623/24 |
| 2015/0112448 | A1* | 4/2015 | Scott | A61F 2/72 |
| | | | | 623/25 |

(Continued)

*Primary Examiner* — Kristen Matter
(74) *Attorney, Agent, or Firm* — Mark S Hubert

(57) ABSTRACT

A body-powered articulated prosthetic hand where each of the segments of the digits, the palmer plate, the thumb pivot plate and the wrist are individually sizeable. This allows for both a proportionately scalable hand as well as individual customization of geometric configurations tailored to specific use patterns. The hand is crushable since it has flexible and pivotable connections between digits along the length and width of the hand. It has a hollow member construction that imparts a strong lightweight design. It is modular so individual parts can be replaced for quick repair. From an aesthetics point, it is visually pleasing and can be offered in different colors, and with custom digit sleeves for specific applications. Fingers can be operated individually or in groups via pairs of cables which allow operation in either voluntary open or voluntary closed modes of control. The flexible construction allows gripping of irregularly shaped objects and deforms before failing giving indication of overload prior to failure.

14 Claims, 21 Drawing Sheets

(56) References Cited

U.S. PATENT DOCUMENTS

2015/0351935 A1* 12/2015 Donati .................... A61F 2/586
                                                    623/25
2016/0367383 A1* 12/2016 Sensinger ............... A61F 2/583
2017/0049583 A1*  2/2017 Belter ..................... A61F 2/583
2018/0036145 A1*  2/2018 Jury ........................ A61F 2/586
2018/0071115 A1*  3/2018 Lipsey .................... A61F 2/582

* cited by examiner

MECHANICAL PROSTHETIC HAND

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

The present invention relates to a novel design for a mechanical hand that introduces a new level of tactile operation for those who need such prosthetic devices. It is adapted to matingly connect with various standardized prosthetic hand/arm components, thereby allowing a simple conversion for existing prosthetic hand users.

BACKGROUND OF THE INVENTION

Despite the portrayal of high tech prosthetic hands as the norm on the media, the current state of the art for prosthetic hands/arms for the average person leaves much to be desired. The most widely used terminal device is known as the "Hosmer™ Hook" and has been around since 1912. The basic Hosmer™ Hook has a single pair of opposable, crescent shaped pinchers. It is a voluntary-open terminal device having a series of elastic bands that keep the pinchers closed. It is body-powered, very reliable, predictable, waterproof, affordable and enables precise grasping of small objects with good visibility of the item being grasped. It is very robust and capable of manipulations with very small items. Unfortunately, it has several drawbacks. It is somewhat menacing to look at, is visually intimidating to third parties, has a limited ability to grasp irregularly shaped or large objects, does not lend itself to disguise with garment cover. While this device performs a single pinching task well, it is limited to manipulations from rigid, non-adjustable, fixed length pinchers rotating in a single plane. Also, this hook looks nothing like a human hand.

Other more sophisticated (e.g. robotic) hands are capable of performing with more dexterity but are also limited in many ways. These five-fingered robotic hands tend to feature complex electro-mechanical assemblies and as such tend to be expensive, fragile and require a silicone glove to be waterproof. They are non flexible, non customizable and frequently incorporate motors or other electrical systems within the hand itself resulting in a stiff monolithic palm which is not scalable and not lifelike. Performance of these hands is limited by battery life. Many of such prosthetic hands are not scalable or available in small sizes for children or women.

Henceforth, an aesthetically appealing, body-powered, five-fingered, prosthetic hand, would fulfill a long felt need in the prosthetic device industry. Similarly, a scalable prosthetic hand that replicated the springy load-bearing flexibility of a human hand would allow for a greater visual and emotional acceptance. This new invention utilizes and combines known and new technologies in a unique and novel configuration to overcome the aforementioned problems and accomplish this.

SUMMARY OF THE INVENTION

In accordance with the invention, the object of the present invention, which will be described subsequently in greater detail, is to provide an improved mechanical hand that is able to connect to the existing body powered harness or to myoelectric controlled systems.

It is another object of the present invention to provide a prosthetic hand that approximates the look and function of the human hand with five digits capable of being manipulated with an opposable thumb capable of adjustable angle opposability.

It is yet another object of the present invention to make a human hand-like prosthetic device wherein each finger digit assembly is made from a series of different sized connected elements so as to allow scalability of the device.

It is still another object of the present invention to provide a lightweight prosthetic hand that can be fabricated from the assembly of a minimal number of components, many identical, each of which can be economically and simply fabricated.

It is a further object of the present invention to provide a prosthetic hand with the capacity for individual digit control.

It is still another object of the present invention to offer a prosthetic hand that has finger digit assemblies that incorporate metacarpal members which laterally-only pivot at their proximal end in a plane that resides approximately 90 degrees relative to the plane of curl or extension of the individual finger digits.

It is a final object of the present invention to offer an improved, robust prosthetic hand capable of providing an entire host of different grasping and holding features configured similar to a human hand so as to present a five-fingered crushable compliant grasping profile that is able to be powered/operated by an industry standard body powered harness.

The improved mechanical/prosthetic hand has many of the advantages mentioned heretofore and many novel features that result in a new human hand-like device which is not anticipated, rendered obvious, suggested, or even implied by any of the prior art, either alone or in any combination thereof.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

BRIEF DESCRIPTION OF THE DRAWINGS

Note: Only FIGS. 5 and 10 show the operational cables. The operational cables have otherwise been removed for diagrammatic simplification and visual clarity. Only FIGS. 1 2, 3, 4, 16 and 18 show the flexible knuckle spacers and passive thumb closing sling. The flexible knuckle spacers and/or passive thumb closing sling have otherwise been removed from FIGS. 3, 4, 17 and 19-21 for diagrammatic simplification and visual clarity.

DETAILED DESCRIPTION

Figure 1:
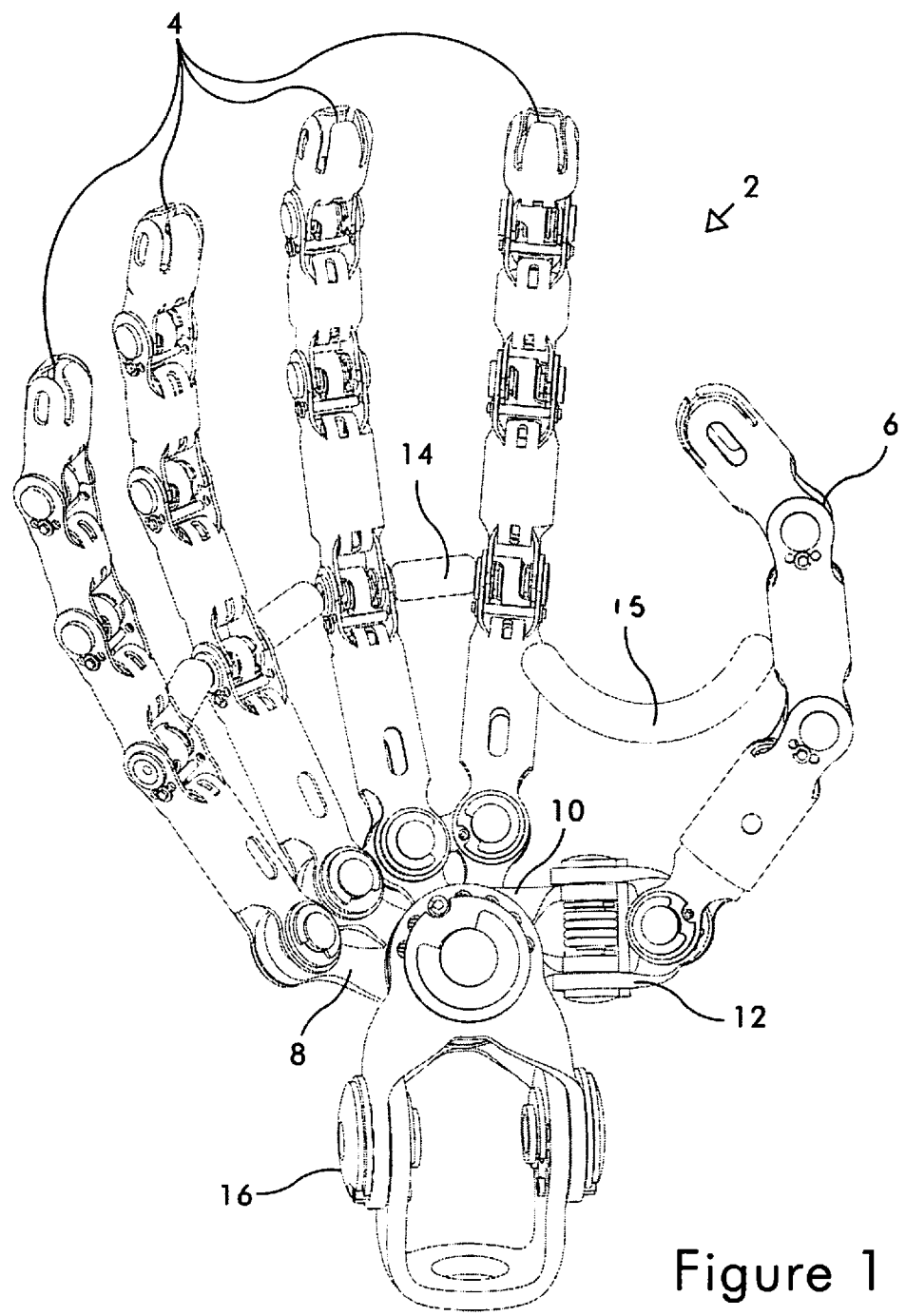
FIG. 1 is a front perspective view of the prosthetic hand with attached flexible knuckle spacers and passive thumb closing sling.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. As an exemplar, the number of digits and type of digit and scalable size of each digit is fully customizable for both prosthetic and robotic applications. Also, it is to be understood that the phraseology and terminology employed herein are for the purpose of descriptions and should not be regarded as limiting.

As used herein, the term "mechanical hand" or "prosthetic hand" refers to a device often referred to as a prosthetic arm. Although discussed herein used as a prosthetic hand, it is known that it may be used in robotics applications or other powered applications as well because of its human hand-like tactile similarities.

For proper understanding of the present invention, it is important to define the "palm" area of the invention, and more specifically the "crushable palm" of the present invention, which distinguishes it from all other prior art. The crushable palm area of the present invention extends from just distal of the wrist, and includes the entire area of the individually moving metacarpal digits, up to and including the flexible knuckle spacers. The metacarpal digits are located at the proximal ends of each finger digit assembly, and also the thumb assembly, and the crushable palm area includes all of these individual metacarpal members. Since these metacarpal digits each pivot at their proximal ends, in a laterally only fashion, and move relative to each other, the palm of the present invention is differentiated from all other prior art prosthetic hands. These lateral-only pivoting metacarpals, all flexibly connected, enable the palm area to be crushable, and it is to this crushable palm that the necessary finger digits are then attached.

All other prior art has palms which are solid blocks, usually with no metacarpal members at all. In prior art, even when metacarpal-like members are present, they are fixed in position, and do not move relative to each other. In other words, in all other prior art, the palm area is an immovable block to which fingers are then attached, with the palm area simply serving as a fixed mounting point for the fingers, or as a solid containment area for motors or systems. By contrast, in the present invention, the palm area is assembled from individual, movable metacarpal members which move relative to each other, enabling compression and a "crushable palm". In the present invention, the entire palm (metacarpal) area is compliant, connected and deformable, while still being load-bearing. Once again, this crushable palm area of the present invention extends from just distal of the wrist, and includes the entire area including all of the individual pivoting metacarpal digits, up to and including the flexible knuckle spacers. The finger digits, are in turn, attached to these moving metacarpals.

The term "crushable" refers to the ability to have the metacarpal digits (the palm) simultaneously laterally-only pivot at their proximal connections to the palmar plate 8 in a plane perpendicular to the plane of the curl of the individual finger digits, and also simultaneously flex slightly about their polymer spacers when external forces are applied. It should be noted that the location of palmar plate 8 of the present invention is (anatomically speaking) at the very bottom of the palm, close to the wrist, with the remaining majority of the palm area being defined by the region containing the movable lateral-only pivoting metacarpal members. The finger digit assemblies, because of their lateral-only pivots at their proximal ends, can be crushed as a group or undergo individual shocks without damage to the hand. By allowing deformation in this way, the present invention provides greater flexibility and compliance for grasping irregularly shaped objects, especially when compared to blocky palms of the prior art. Importantly, the laterally-only pivot points of the present invention, by virtue of their limited movement, are also therefore load-bearing in directions perpendicular to their allowed movement. In this way, the palm area remains crushable, as described above, while still maintaining necessary load-bearing capacity when forces are applied perpendicular to the lateral-only plane of crushability. This load-bearing capacity is of great importance for real-world use by amputees.

It is to be noted, that because of the similarities between the prosthetic hand and the human hand, much of the medical terminology of the human hand has been adopted for the designations of the various elements of the device.

The improved prosthetic hand 2 has been modeled after the human form with four scalable finger digit assemblies, and one scalable thumb digit assembly. Each of these is separately capable of dorsal extension (finger opening) and palmar flexion (finger closing) and with the ability to be individually controlled as desired.

Figure 2:
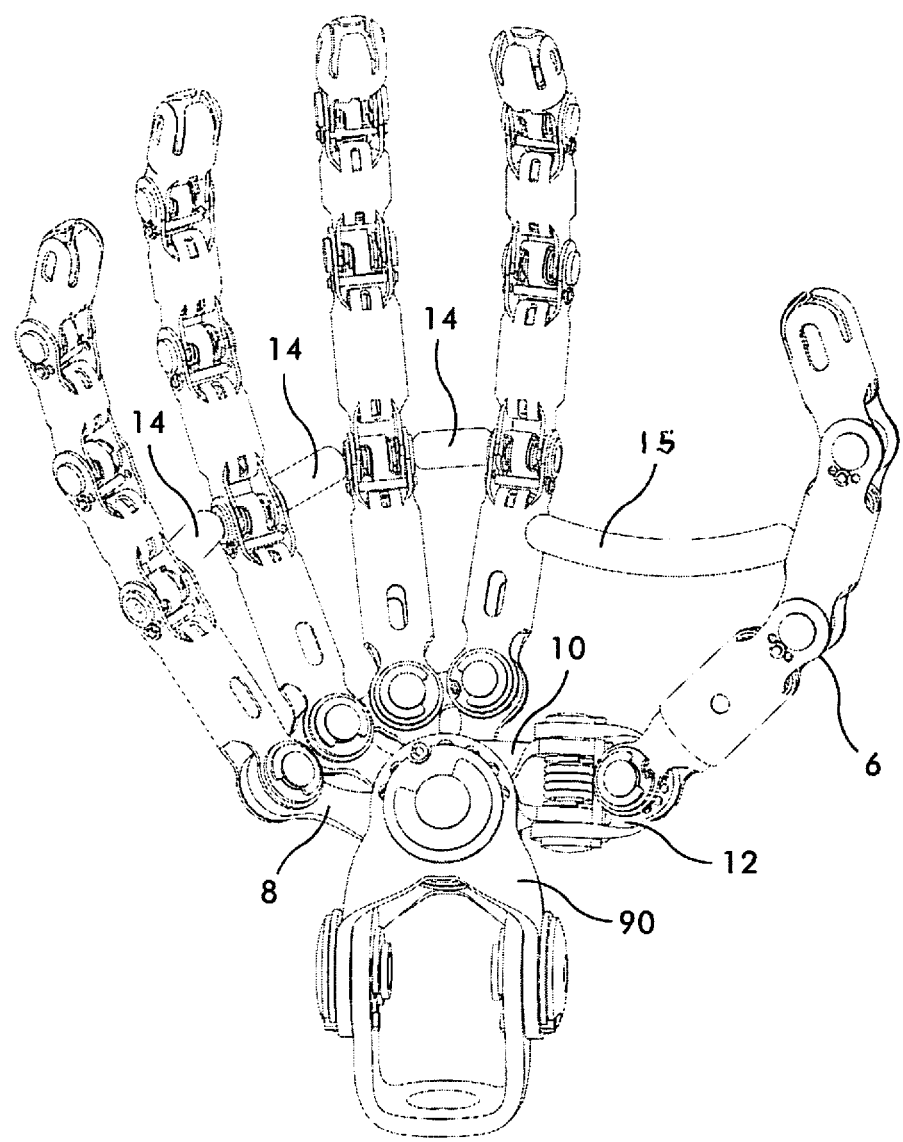
FIG. 2 is a front perspective view of the prosthetic hand with attached flexible knuckle spacers and passive thumb closing sling.

Looking at FIGS. 1 and 2, it can be seen that the hand 2 has eight main parts: the finger digit assemblies 4; the thumb digit assembly 6; the palmar plate 8; the thumb rotation plate 10; the thumb pivot flange 12; the flexible knuckle spacers 14; passive thumb closing sling 15; and the wrist 16.

The palmar plate 8 is the central hub or means for operationally supporting all of the finger digit assemblies 4 and thumb digit assemblies 6 for digital movements. It also mounts to the wrist 16 for operational connection to the user.

The hand 2 is designed to be a terminal device wherein it is affixed to a standard prosthetic socket that mounts to the distal end of the user's residual limb. Generally, a socket is fitted on the residual limb and connects the residual limb to the prosthetic device 2. These sockets are attached by a tight, custom friction or vacuum fit over the residual limb. The connection of the prosthetic hand 2 to the residual limb is not discussed herein. There are several different matingly engageable mechanical configurations that may be utilized, each of which is commercially available. Adaption of the prosthetic hand to any of these devices is merely an act of mechanical manipulation as would be well known by one skilled in the art.

Operation of the prosthetic hand may be via one of the common cable and sling arrangements that are typically worn up the arm and across the shoulders of the user (body powered). Optionally, the prosthetic hand 2 may be operated by motorized driven myoelectric control initiated by a signal. Such signals may come from an electrical impulse generated by an electrode operationally contacting a muscle group, (e.g. in the forearm). It is to be noted that when used as a human prosthetic device, the hand 2 is designed to have a palm that is crushable, having flexible knuckle spacers 14 between the distal ends of the metacarpal digits 24 along the width of the hand 2. The connection of these flexible knuckle spacers 14 to the metacarpal digits 24 limits the movement of the metacarpal digits 24 relative to one another and as a group. The flexible knuckle spacers 14 in the preferred embodiment are simply flexible cables sheathed with a pliable polymer between the sections spanning adjacent digits. There are flexible knuckle spacers 14 spanning between adjacent digit assemblies between the pinky digit assembly 34 and index digit assembly 28. (Although there may be more or less flexible knuckle spacers 14 to accomplish the desired functionality of the hand 2.) As stated, there are lateral-only pivotal connections at the base of each finger digit assembly 4 and the thumb digit assembly 6. This synergistic design of lateral-only pivoting finger digit assemblies 4 and flexible knuckle spacers 14 allows for the "crushable palm" feature of the hand 2 and prevents irreparable harm to the hand or its components under unexpected mechanical loads or shock. Additionally, the flexible knuckle spacers 14 between all digits along the width of the hand 2, allows simultaneous limited motion of some or all of the finger digit assemblies 4 with respect to the other finger digit assemblies 4, or the thumb digit assembly 6.

The prosthetic hand 2 has numerous physical configurations so that it can be individually customized for each user or for specific tasks that the user may be attempting. One such example can be seen in FIGS. 3 and 4 where it can be seen that the thumb digit assembly 6 utilizes a tube-in-tube sleeved configuration that allows the adjustable, mechanical fixation of the thumb digit assembly through a full range of rotations, as will be discussed in detail herein.

Figure 4:
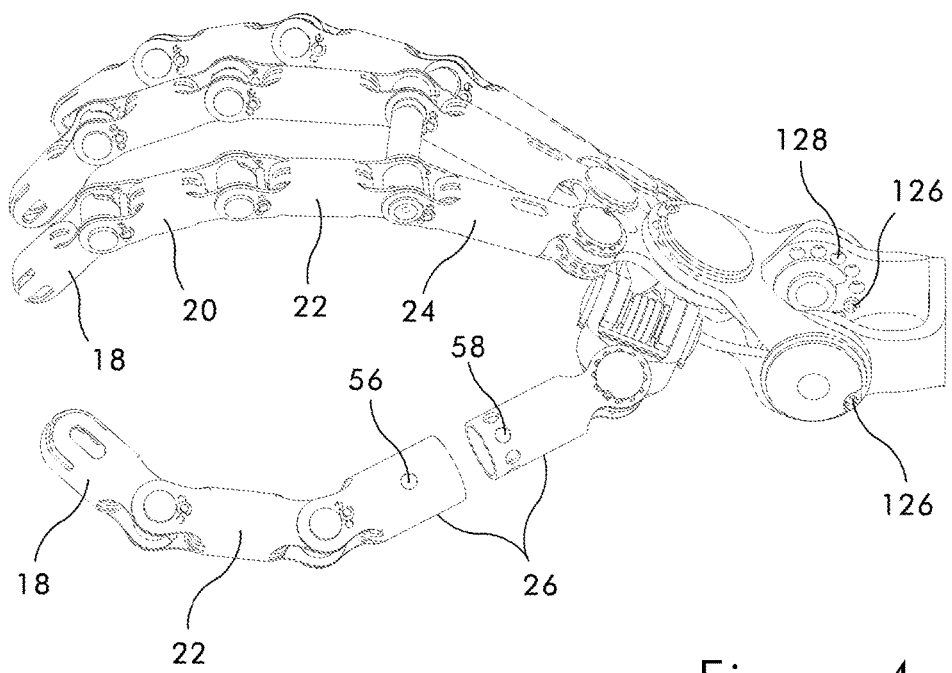
FIG. 4 is a side perspective of the prosthetic hand.
Figure 5:
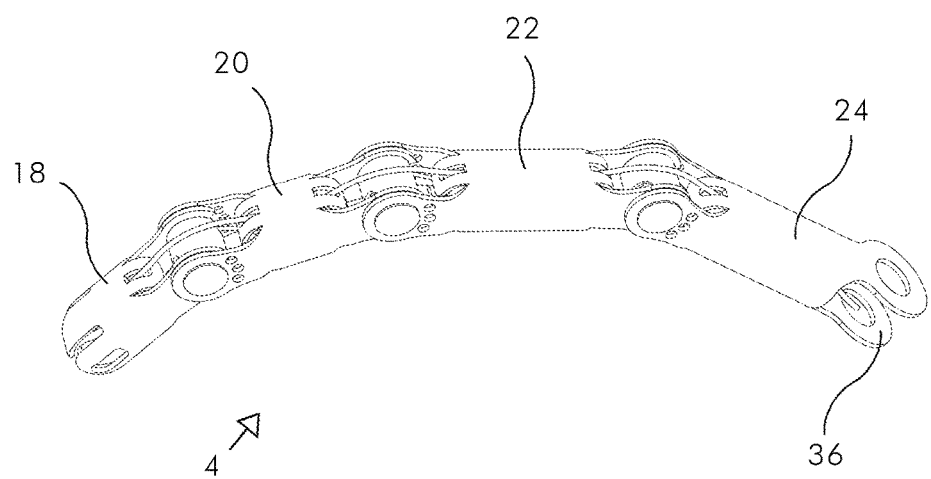
FIG. 5 is a top perspective view of a finger digit assembly, flexed.
Figure 6:
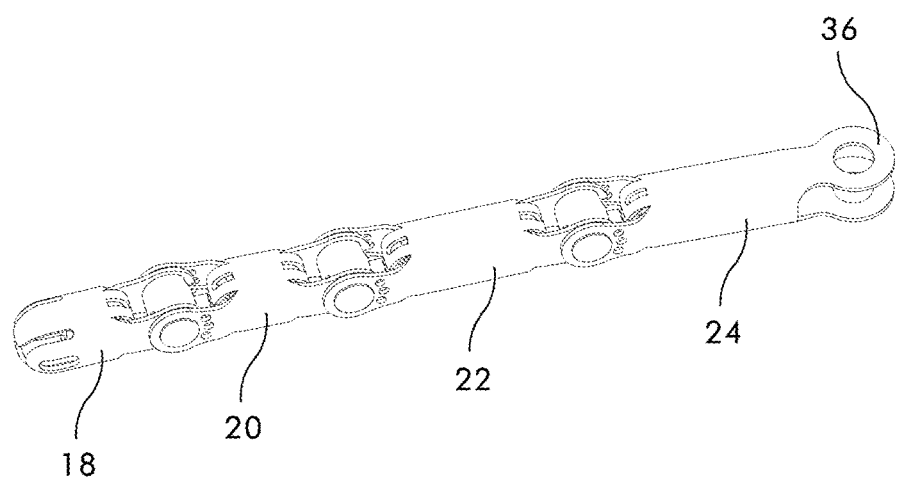
FIG. 6 is a side perspective view of a finger digit assembly, straightened.

Looking at FIGS. 4-6 it can be seen that the four digit assemblies 4 approximate the digits of the fingers, plus one metacarpal digit, and as such have a total of four separately scalable individual elements pivotally connected in a linear (series) fashion from a distal phalange digit 18 at the tip, a middle phalange digit 20, a proximal phalange digit 22 and lastly a metacarpal digit 24. The fifth digit assembly approximates a thumb (thumb digit assembly 6) and resembles the finger digit assemblies but lacks a middle phalange digit 20 and also has an axially adjustable thumb metacarpal digit 26. Except for the elimination of the middle phalange digit 20 in the thumb digit assembly 6 and the axially adjustable thumb metacarpal digit 26, the finger digit assembly 4 and thumb digit assembly 6 structures are functionally identical. Generally, the thumb digit assembly 6 is the shortest of the digit assemblies. Each of the digit assemblies is capable of independent curling or straightening. Again it is noteworthy to state that the length, width and thickness of the individual digit assemblies is variable as well as the number of phalange digits used to construct the digit assemblies. (The ability of curling or straightening of the finger digit assemblies 4, in addition to their ability to laterally-only pivot at the proximal end of their metacarpal digits 24 in a plane that lies approximately 90 degrees relative to the plane of curl or extension of the individual finger digits, is one of the distinguishing and novel features of this hand.)

From the thumb digit assembly 6 outward, the four finger digit assemblies 4 are named as follows: index digit assembly 28, middle digit assembly 30, ring digit assembly 32 and pinky digit assembly 34 (see FIG. 5).

The proximal phalange digit 22 of the thumb digit assembly 6 is connected to the index finger digit assembly at its metacarpal digit by a passive thumb closing sling 15. In the preferred embodiment, this passive thumb closing sling 15 is made of a cable held in a spring like fashion by a flexible polymer covering. This acts like the human hand's adductor pollicis and flexor pollicis brevis muscles so as to flexibly span the space between the thumb digit assembly 6 and index digit assembly 28, passively drawing the thumb digit assembly 6 towards the palm, when pressure is applied, without input from the control cables, (e.g. grabbing a broom handle). The proximal ends of each of the finger digit assemblies 4 (the proximal ends of the metacarpal digits) terminates in a parallel pair of generally planar, substantially similar palm flanges 36. These palm flanges 36 lie in a plane that is generally perpendicular to the plane in which the individual finger (phalange) digits curl, and have a connector orifice formed therethrough. Generally, this is also true of the thumb digit assembly 6 however, as discussed earlier, the thumb digit assembly 6 has an axially adjustable thumb metacarpal digit 26. These palm flanges 36 are what connect the thumb digit assembly 6 and finger digit assemblies 4 to the palmar plate 8 and because of their perpendicular orientation with respect to plane of the finger curl, allow the finger digit assemblies 4 and thumb digit assembly 6 to pivot in the same plane of the palmar plate 8 so as to allow the individual finger or thumb digit assemblies to adjust their proximity to adjacent finger or thumb digit assemblies and to pivot laterally only, thereby imitating human hand structure and allowing overall palm crushability of the hand 2.

Figure 7:
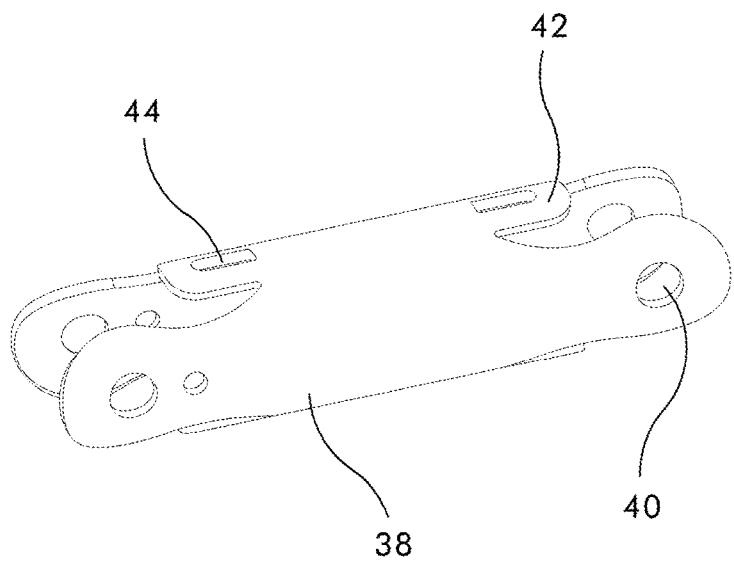
FIG. 7 is a side perspective view of a phalange digit tube, partially formed.
Figure 8:
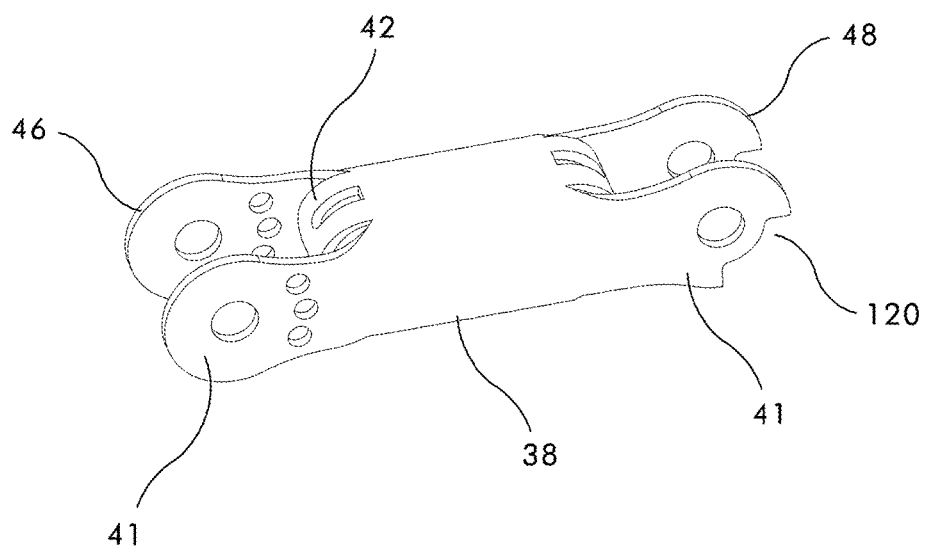
FIG. 8 is a side perspective view of a phalange digit tube, fully formed.
Figure 9:
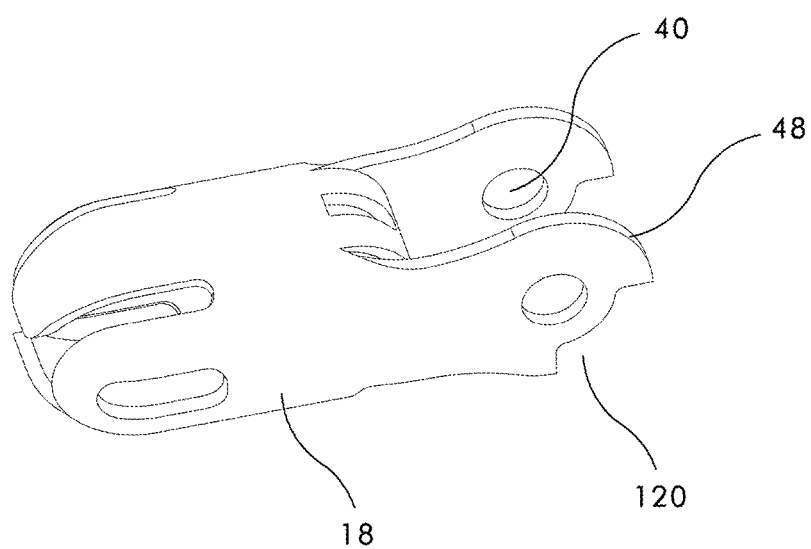
FIG. 9 is a side perspective view of a distal phalange digit.

FIGS. 7-9 illustrate the most important individual components of the digit assemblies—that of the individual digit tube sections. Each of the phalange digits and metacarpal digits are made from a short tube section 38 cut or stamped and formed, or 3-D printed to a specific configuration. FIG. 7 shows the first stage of the construction of a tube section 38. The phalange digits and metacarpal digits need not be formed from the same diameter tubing. In one embodiment the tubing is oval or circular, thin walled (0.030 in outer diameter wall thickness in the preferred embodiment) having a ½ inch outer diameter finger digit assemblies 4 and the distal end of the thumb metacarpal digit 26 and a ⅝ inch outside diameter for the proximal end of the thumb metacarpal digit 26. Each end (distal or proximal) of the tube section 38 has a pair of opposing pivot pin orifices 40 formed there through at 180 degrees apart. Between the pair of pivot pin orifices 40, there resides a pair of opposing cable guides 42 formed by the absence/removal of tube wall sections there between the pivot pin orifices 40. Since the cable guides 42 terminate before the ends of the tube section, the distal and proximal ends of the tubes have parallel, opposing coupling flanges 41, through the center of which are the pivot pin orifices 40. It is these coupling flanges 41 that allow the relative motion of adjacent tube sections. Each opposing cable guide 42 has a cable slot 44 there through and is much shorter than the coupling flanges 41. The coupling flanges 41 all reside generally parallel to the same plane except those at the proximal end of the metacarpal digits, which are perpendicular to the other coupling flanges.

FIG. 8 shows the second stage of construction where it can be seen that the ends of the four cable guides 42 are bent in an arc toward the longitudinal centerline of the tube section 38. Additionally, the distal end 46 and proximal end 48 of the tube section 38 are bend inward toward the tube section's center in a planar fashion about an axial planar bend line about the tube section 38 that also defines the beginning of the bend of the cable guides 42.

Figure 17:
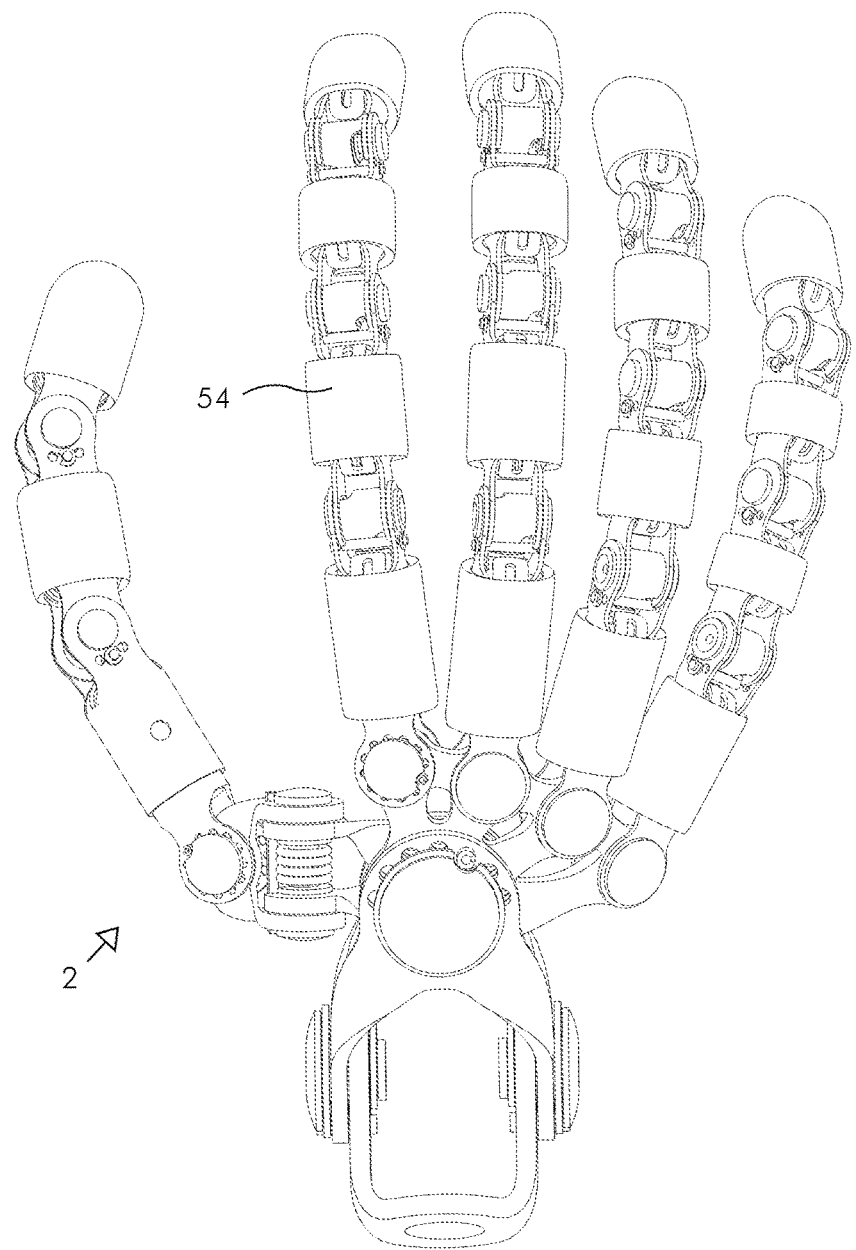
FIGS. 17-21 are front and rear perspective views of the prosthetic hand showing various finger, thumb and palm positions, and crushable palm.
Figure 18:
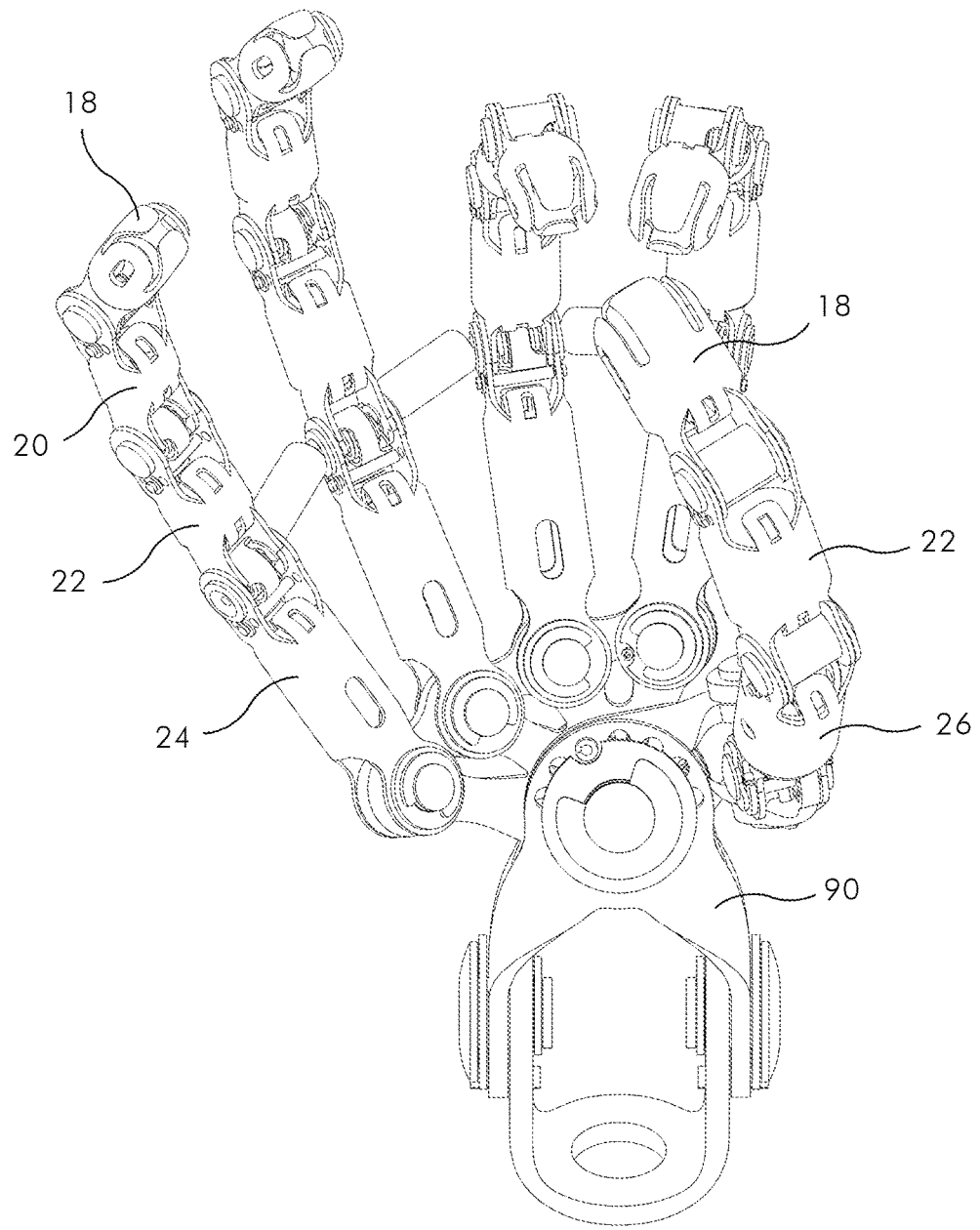
Figure 19:
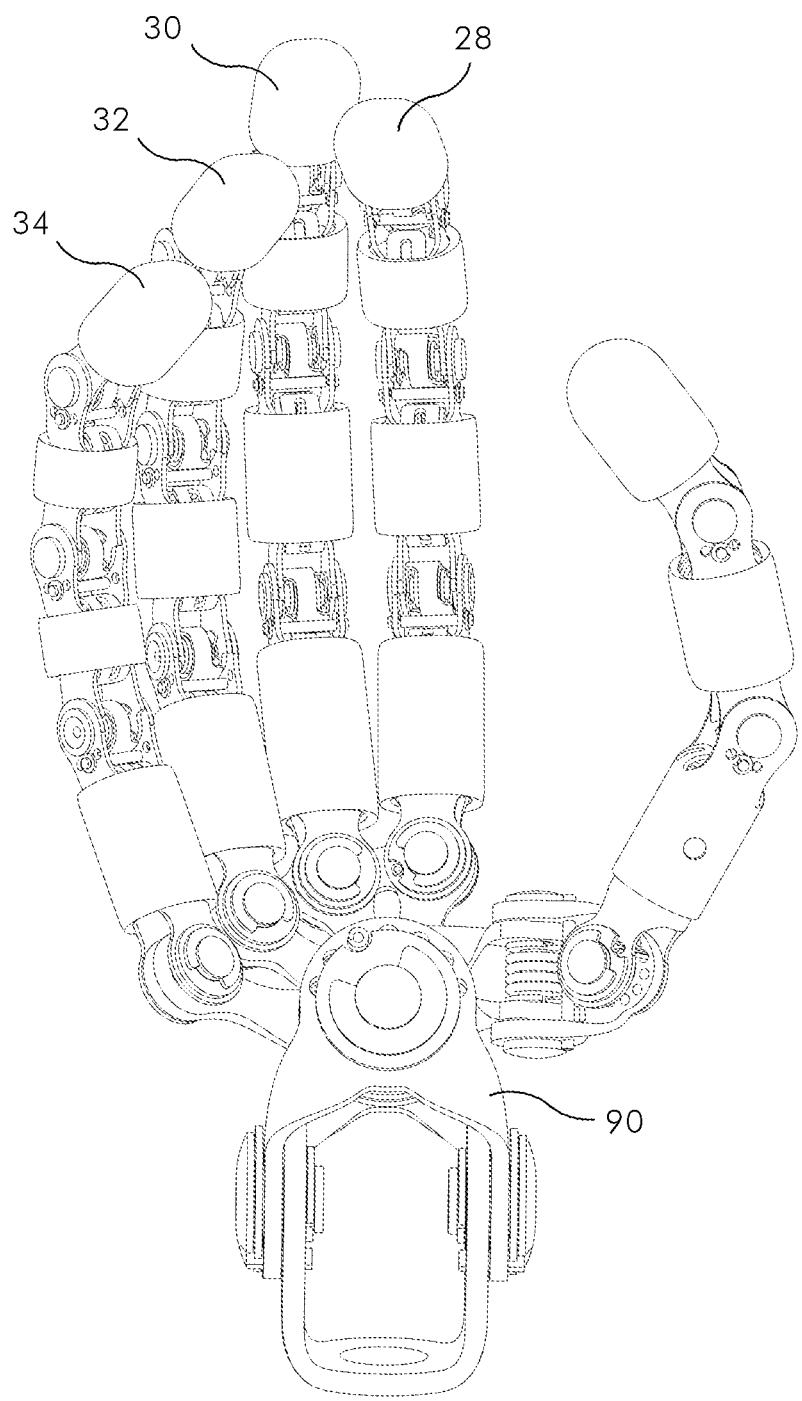
Figure 20:
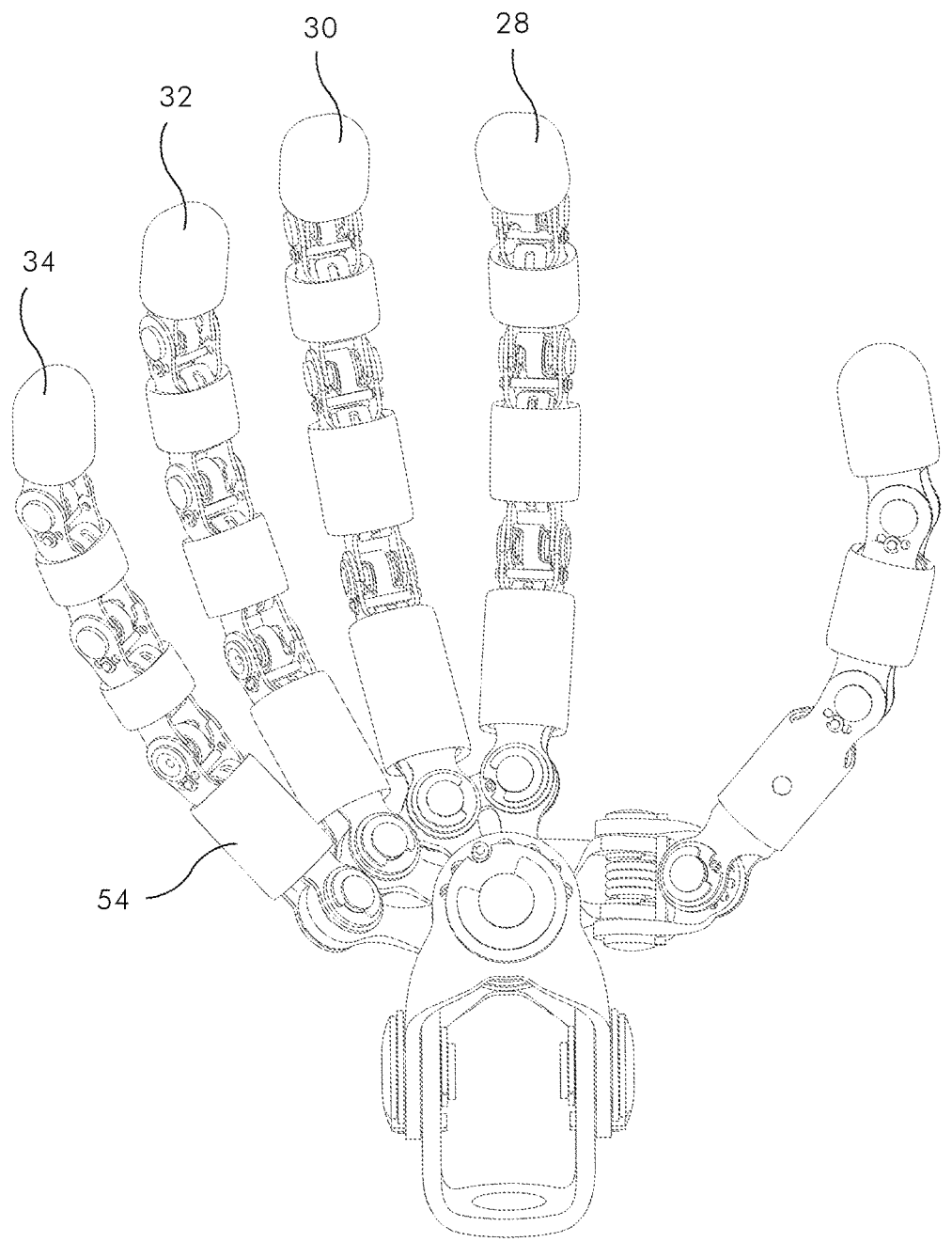
Figure 21:
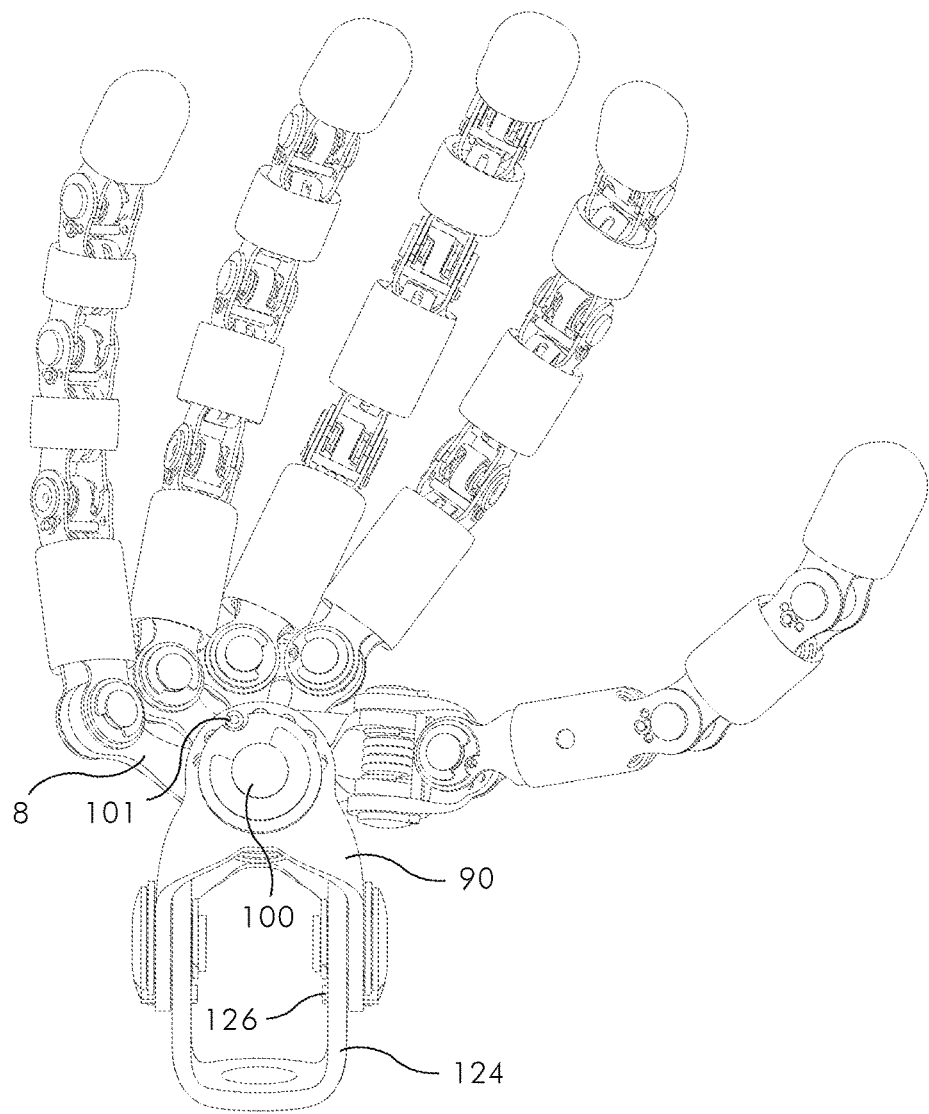

Looking at FIGS. 5 and 6 it can be seen that the distal phalange digit 18 differs from the middle phalange digit 20, and proximal phalange digit 22 because its distal and proximal ends are not identical. Rather, at the distal end, the entire distal end of the tube is bent towards the tube's longitudinal centerline so as to approximate the shape of a fingertip. An optional fingernail may be affixed to this distal phalange digit. Similarly, an optional polymer sleeve 54 (FIG. 17) may be placed around the outside of the tube sections 38 for aesthetics and functional reasons.

Figure 16:
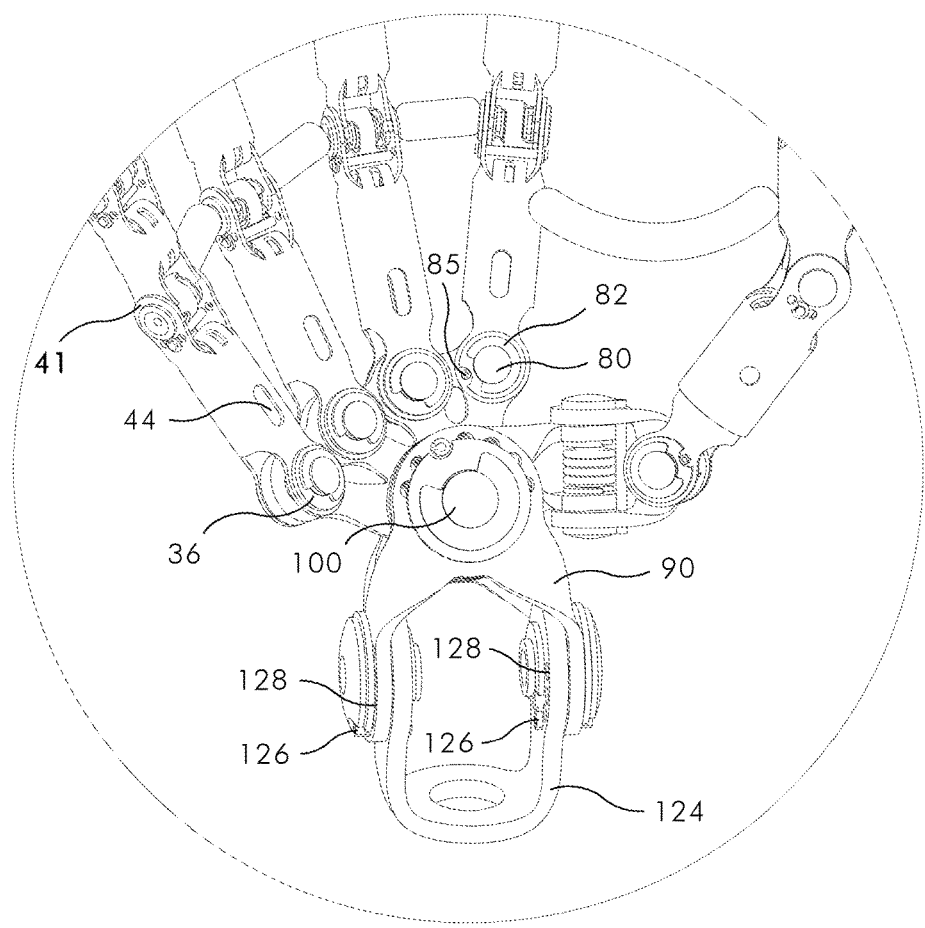
FIG. 16 is front perspective view of the installed prosthetic hand index finger digit locking assembly.

The finger metacarpal digits 24 and the thumb metacarpal digit 26 have a similar but slightly different structure than the phalange digits, although still based on the tube section design. In FIG. 16 it can be seen that the tube section still retains the two parallel coupling flanges 41 at its distal end, however at the proximal end, there are two parallel palm flanges 36. The plane of the palm flanges 36 reside perpendicular to the plane of the coupling flanges 41. These palm flanges 36 enable laterally-only movement of the metacarpal digits 24 and thumb metacarpal 26. This lateral-only pivoting of the palm flanges 36 accounts for the ability of the metacarpal digits (the palm) to be load bearing in one plane while still allowing for the crushable palm feature in another plane. Also, there are no cable guides 42 at the proximal ends of the metacarpal digits 24 or thumb metacarpal digit 26. Rather, there are cable slots 44 on the palmar and dorsal sides of the metacarpal digits 24 to allow passage of cables. The coupling flanges 41 and palm flanges 36 are substantially similar but for their orientation on the tube section. The palm flanges 36 also have centrally located pivot pin orifices 40 formed therethrough.

Figure 3:
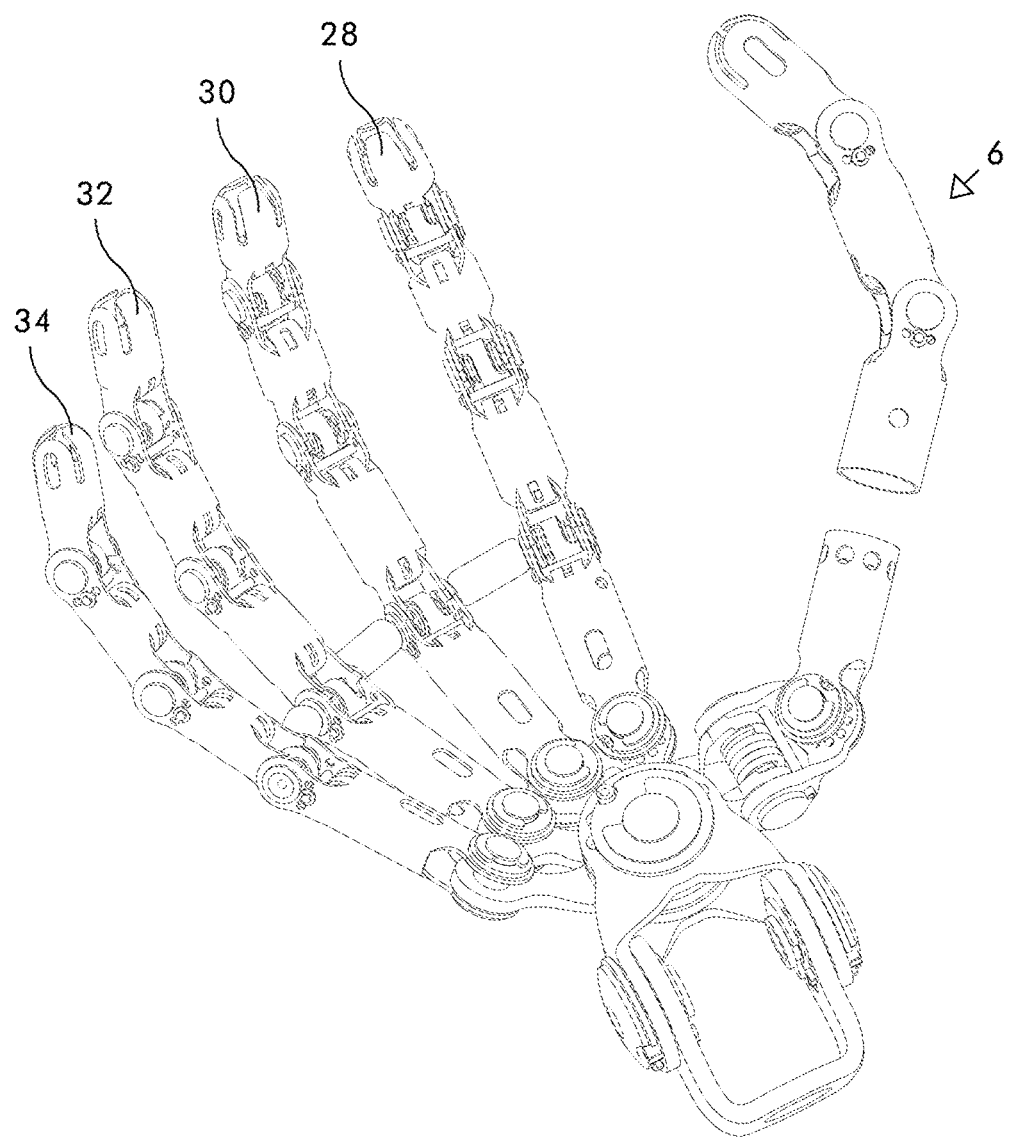
FIG. 3 is a front perspective view of the prosthetic hand with an exploded thumb.

The structure of the thumb metacarpal digit 26, as shown in FIGS. 3 and 4, is slightly different to allow for the thumb digit assembly 6 to axially adjust. In this manner it may oppositionally contact any desired finger digit assembly, as desired by the user. The thumb digit assembly 6, when straightened, has a linear axis that it is rotatable about so as to enable adjustable-angle opposable contact with at least one of the finger digit assemblies. To accomplish this, the thumb metacarpal digit 26 has a two-piece tube construction rather than a single tube section 38. It resembles a finger metacarpal digit 24 that has been cut perpendicular to its long axis. The distal half of the thumb metacarpal digit 26 has a pair of opposing adjustment orifices 56 formed therethrough. The proximal half of this the thumb metacarpal digit 26 has a series of radially drilled orifices 58 therethrough. The proximal half has an outer diameter sized for frictional but sliding rotation within the slightly larger inner diameter of the distal end 46. When assembled, two of the radially drilled orifices 58 will align with the two adjustment orifices 56 for the insertion of a mechanical fastener. This allows the fixable, axial adjustment of the thumb digit assembly 6. Although in alternate embodiments, other rotational locking devices may be utilized.

Figure 11:
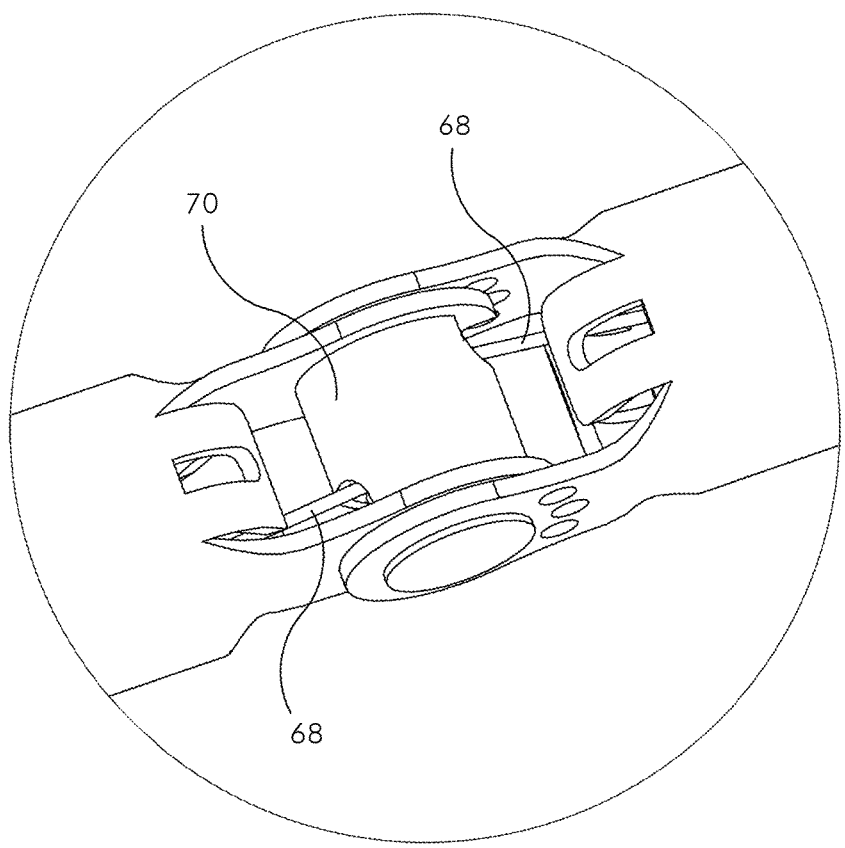
FIG. 11 is a close up top perspective view of two connected phalange digits.
Figure 12:
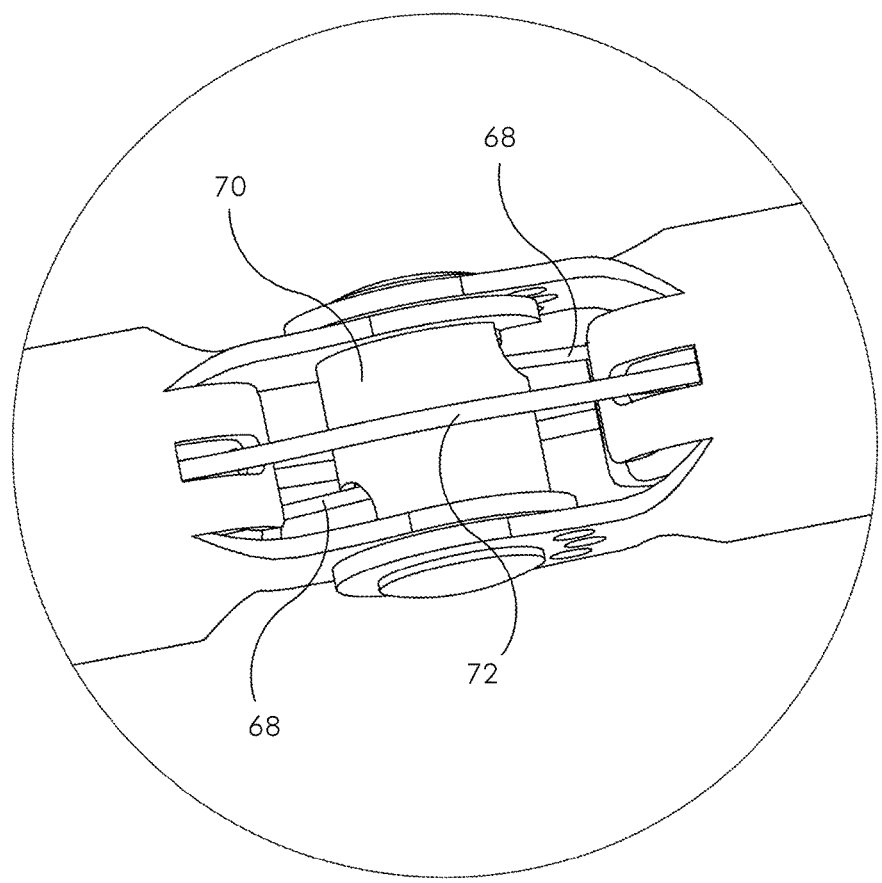
FIG. 12 is a close up top view of two connected phalange digits.

Each of the four finger digit assemblies 4 is assembled from individual finger digits as follows: The proximal end of the distal phalange digit 18 is connected to the distal end of the middle phalange digit 20, and the proximal end of the middle phalange digit 20 is connected to the distal end of the proximal phalange digit 22, and the proximal end of the proximal phalange digit is connected to the distal end of the metacarpal digits 24 (or thumb metacarpal 26) in the identical manner outlined above to facilitate the linear assembly of the digit assemblies (finger digit assemblies 4 or thumb digit assembly 6). In the case of the thumb digit assembly 6, the middle phalange digit 20 is eliminated and the distal phalange digit's proximal end is connected to the distal end of the proximal phalange digit 22. The assembly of the individual phalange digit-to-phalange digit connections, and phalange digit-to-metacarpal digit connections of the finger digit assemblies 4 and thumb digit assembly 6, are best explained in FIGS. 10-12 with reference to the connection between a distal phalange digit 18 and a middle phalange digit 20. It is to be noted that each of the finger and thumb digit assemblies (and thus the entire hand) are scalable because each of the individual phalange digits are available in differing lengths and each finger or thumb digit assembly may be made of a customized array of different sized individual phalange components.

Beginning with a distal phalange digit 18, the two coupling flanges 41 at the proximal end 48 of the tube section are fitted adjacent to (within) the two coupling flanges 41 at the distal end 46 of the middle phalange digit 20 such that their pivot pin orifices 40 align. Through one set of aligned pivot pin orifices 40 is inserted a first pivot pin 60. The pivot pin 60 is less than one half of the width distance between the parallel connection flanges 41 of a tube section 38. Each pivot pin 60 has a head that resides normally to a shaft section that has an axial groove 64 formed therein, sized to accept a circular retaining clip 62. These are commercially available mechanical fasteners, well known in the art. A retaining clip 62 is placed in the axial groove 64 in the pivot pin 60 such that the inner face of the retaining clip 62 resides adjacent to the inner face of the proximal end 48 of the distal phalange digit 18. A (wound) torsion spring 66 is placed over the shaft section of the pivot pin such that its two spring legs 68 (that reside 180 degrees apart and at opposite ends of the spring body) are constrained by the inner wall of the tube sections 38 of the connected phalange digits or metacarpal digits. (These spring legs 68 are long enough to extend into the internal cavity of the tube section 38.) A spring cover 70 is placed over the torsion spring 66 and the underlying shaft section of the first pivot pin shaft section, and a second pivot pin 60 is installed and affixed through the second set of aligned pivot pin orifices 40 in the distal phalange digit's proximal end 48 and the middle phalange digit's distal end 46 in an identical fashion as described above. The spring cover 70 merely prevents the cable 72 from interfering with the torsion spring 66. It is to be noted that the torsion spring 66 may be oriented such that the torsional spring legs 68 may either open or close the joint. In other words, by changing the orientation of the torsion springs 66, and repositioning the tension cable 72, the present invention can be configured such that pulling the tension cable 72 serves to either open or close the fingers, as needed by the user.

The closing order of individual phalange digits is determined by the strength of the respective torsion springs 66 selected for use in that specific phalange digit. More specifically, the strength of the torsion springs 66 decrease toward the distal end of the digit assemblies, resulting in a more life-like hand closing profile, wherein the distal ends of the fingers begin curling first because of their lower spring strength. By contrast, it would be undesirable for a finger to close first at its big knuckle, next to the wrist, as this is not life-like. The Applicant's device, in its preferred embodiment, allows adjustment of these torsion springs 66 as desired by the user.

Figure 10:
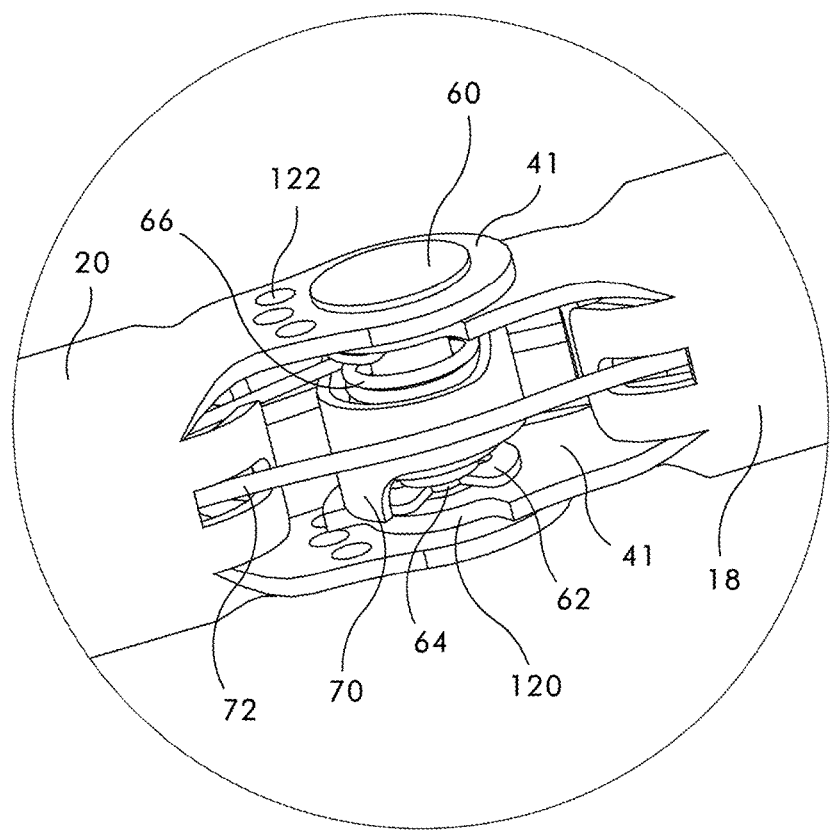
FIG. 10 is a close up bottom perspective view of two connected phalange digits.

Looking at FIGS. 8, 9 and 10, there is peripheral detent section 120 cut in the perimeter of the coupling flanges 41 on the proximal end of the phalange digits. These act in conjunction with an adjustable stop pin (removed for visual clarity) that is installed in one of a series of stop pin orifices 122 formed there through the distal ends of the coupling flanges 41 of the metacarpal digits and phalange digits. This system of stop pins and detents allows for control of the range of motion of the individual finger digits and serve as backstops (e.g. to prevent hyperextension.) This backstop feature combined with the lateral only pivot capability at the proximal ends of the finger digit assemblies ensure that the entire hand assembly 2 is load-bearing in ways that are useful to the user. That is to say, the palm can withstand loading forces from both palmar and dorsal directions because of the lateral-only pivot of the palm flanges 36, and each finger digit assembly, can in turn, withstand loading forces from the palmar side because of the stop pin orifices 122, detents, and stop pins which form backstops for each individual digital connection. At the same time, and even while holding a load, both the palm area and finger digit assemblies still remain crushable in a lateral (sideways) direction, as permitted by the lateral only pivot of the palm flanges 36. The limited allowable motions of the lateral-only pivoting palm flanges on the metacarpals, combined with the backstops in each individual finger digit provide necessary load-bearing strength of the entire hand assembly 2, while maintaining the desirable deformability of the system as a whole, and in particular, the crushable palm.

The remaining connections of the metacarpal digits 24, proximal phalange digits 22, and middle phalange digits 20 are similarly made. The cable 72 is routed through cable guides 42 traversing the linear arrangement of metacarpal digits and phalange digits, passing through the internal cavity of each tube section 38 and the consecutive cable slots 44. The distal end of each cable 72 is affixed to the distal end of each distal phalange digit 18.

It is to be noted that the cable system used to operate the finger digit assemblies 4 and thumb digit assemblies 6 may be of two different configurations. The first configuration (preferred embodiment) uses two cables 72, one internally traversing the dorsal side and one individually traversing the palmar side of each of the digit assemblies. The cables 72 then pass over the palmar plate 8 and are operably connected at their proximal end to the user's preferred control system. (e.g. body-powered or myoelectric) The second configuration utilizes but one cable routed through either the palmar or dorsal side of the digit assemblies and similarly operationally connected as above. Where only one cable 72 is provided, the torsion springs 66 serve to return the finger digit assemblies 4 to the open or closed position depending on whether the cable runs on the palmar side and closes the finger digit assembly 4, or the dorsal side and opens the finger digit assembly 4. (In this way the hand 2 can be configured to operate in either the 'voluntary open' or 'voluntary closed' modes.) The thumb digit assembly 6 is actuated in a similar fashion to the finger digit assemblies 4.

The stiffness of the torsion springs 66 are set for differing tensions across the various phalange digits (each phalange digit relative to the adjacent phalange digit) so as to control the closing profile of the entire hand similar to that of the human form or as desired. Generally, the torsion springs 66 are configured with the weakest spring tension (stiffness) at the distal end of the distal phalange digit and increasing gradually toward the proximal end of the proximal phalange digit.

Looking at a single-cable 'voluntary-close' (cable tension to close) configuration, a single cable 72 on the palmar side of the finger digit assemblies 4 and thumb digit assemblies 6 under tension actively draws the digit assemblies inward in flexion. Since each joint is held extended by differing spring tensions, when the cable 72 is tensioned, the finger digit assemblies 4 and thumb digit assembly 6 curl inward first from the distal end, in a human-like fashion where the joints with the weaker spring forces begin to curl inward first. In this 'voluntary-close' configuration, all joints passively spring open when the palmar cable tension is relieved.

If a single-cable, 'voluntary-open' (cable tension to open) system is employed, the single cable on the dorsal side of the finger digit assemblies 4 and thumb digit assembly 6 under tension draws the digit assemblies outward in extension to open the hand, and the torsion springs 66 serve to automatically close the digit assemblies in flexion, closing the hand.

In a dual cable system, the tension of either cable (dorsal or palmar) actively controls both the flexion or extension of the finger digit assemblies 4 and thumb digit assembly 6. Wherein there is no or reduced dorsal cable tension, the torsion springs 66 again act to control either the opening or closing profile of the digit assemblies.

Figure 13:
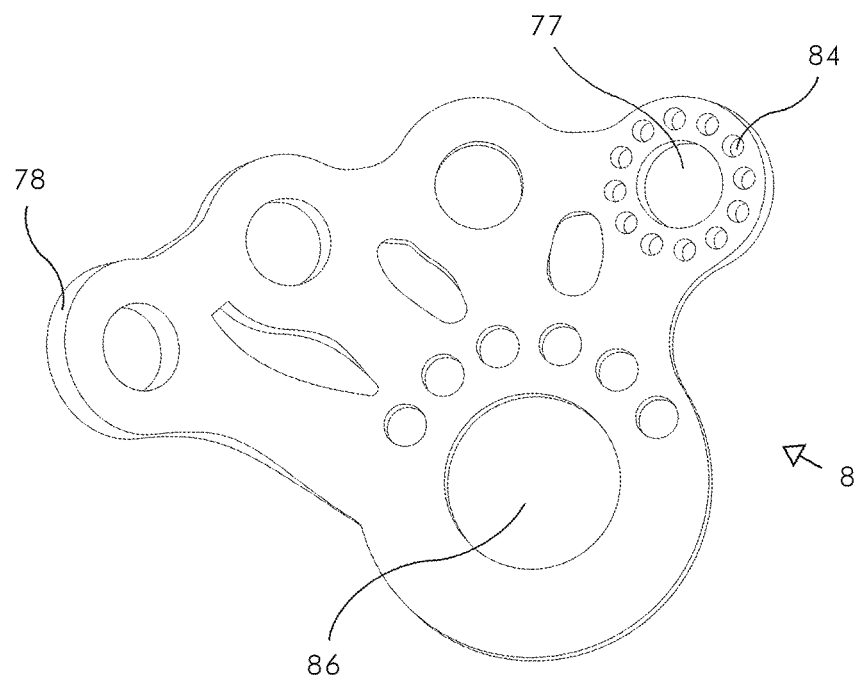
FIG. 13 is a front perspective view of the palmar plate.

FIG. 13 illustrates the means for operationally supporting all of the digit assemblies for digital movements (palmar plate 8). This is a curved plate that acts as the anchor point for the proximal end of the finger metacarpal digits 24 (directly) and the thumb metacarpal digit 26 (indirectly) as well as the connector to the wrist 16. The palmar plate 8 has a series of metacarpal orifices 77 (usually four in number, one for each finger digit assembly 4) formed therethrough that lie in a row adjacent the top perimeter edge 78. Looking at FIG. 16, it can be seen that these metacarpal orifices 77 accommodate the connection of the finger digit assemblies by alignment with the pivot pin orifices 40 in the palm flanges 36 so that a pin 80 with a groove to retain circlip (or e-clip) 82 may be inserted into the aligned orifices. It is known that other mechanical connectors could be optionally used here. Optionally, there may be a flexible, slightly compressible polymer disc (plain bearing) placed between either or both of the palm flanges 36 and the palmar plate 8 to aid and silence pivotal movement of the finger metacarpal digits 24, as well as increase the overall digit flexibility or deflection. More specifically, the purpose of the compressible polymer discs is to deliberately introduce a small amount of flexibility to the lateral-only pivot of the palm flanges 36. In this manner of connection, and with the flexible knuckle spacers 14, the four finger digit assemblies can be lateral-only pivoted as a group on the palmar plate 8. The index metacarpal orifice 77 has a series of lock orifices 84 arranged radially about it. These allow the temporary locking of the index digit assembly in a specific position and relative to the thumb digit assembly 6 and the palmar plate 8 to accomplish a mechanical endeavor. This positioning is accomplished with a mechanical member 85 that passes through the lock orifices 84 and an orifice in the palmar flange 36 of the index metacarpal digit 24, (not visible in figures). Locking the index digit assembly 28, as described above, results in increased rigidity of the index digit assembly, as desired by the user, in order to perform a specific task. It is worth noting that even when the index digit assembly 28 locked into position in this way, the palm remains crushable, as all other finger digit assemblies are still free to laterally-only pivot.

Figure 14:
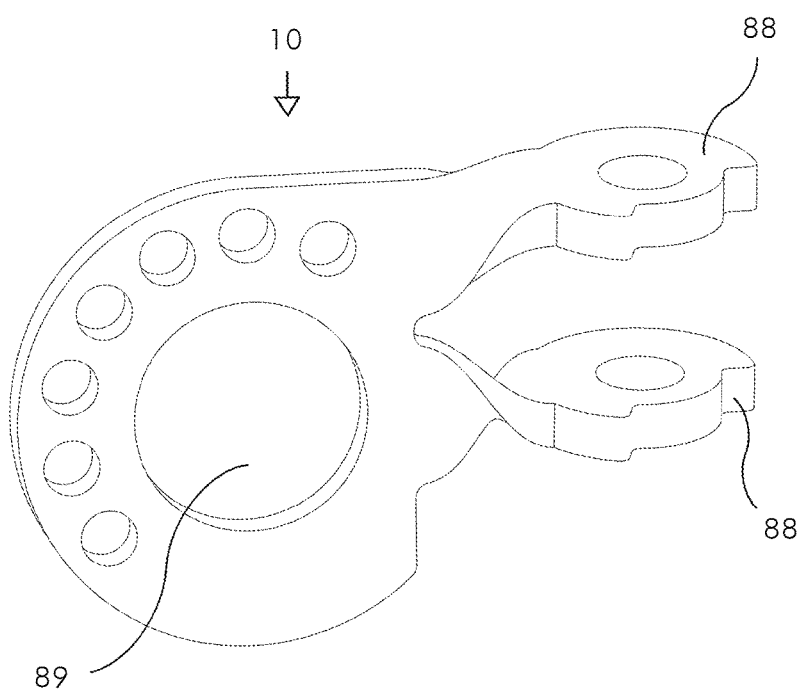
FIG. 14 is front perspective view of the thumb pivot flange.
Figure 15:
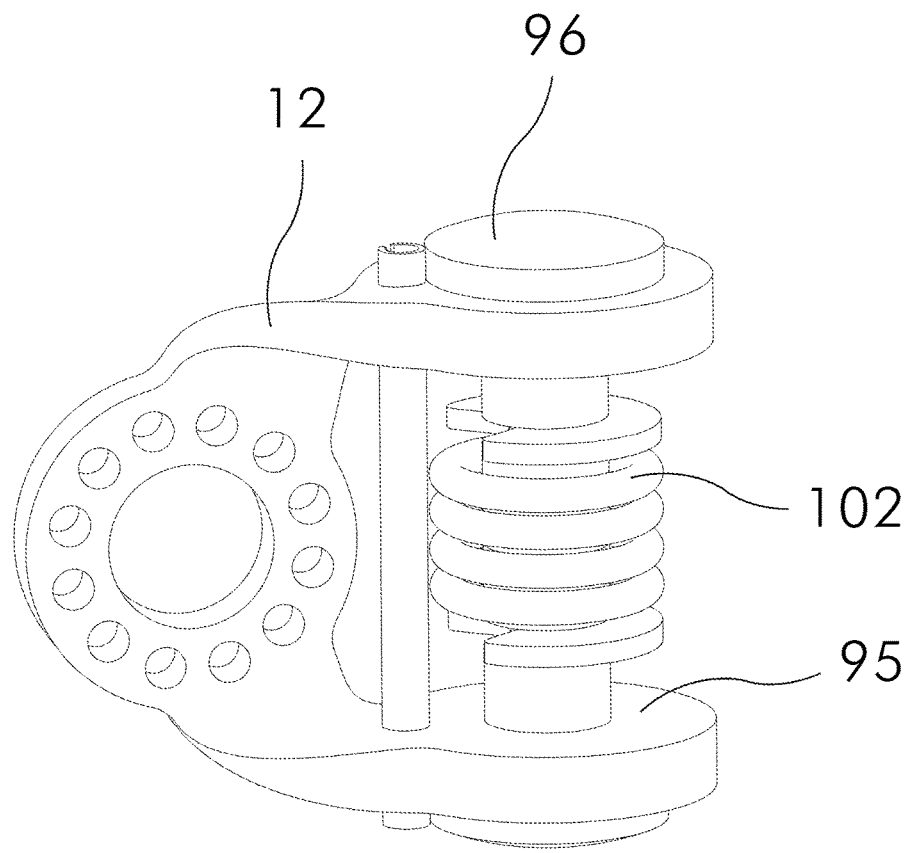
FIG. 15 is a front perspective view of the thumb rotation plate.

On the palmar plate 8 there is also a central orifice 86 that allows the connection of the wrist top bracket 90 and the thumb rotation plate 10. The thumb rotation plate 10 (FIG. 14) with a central opening 89 and a pair of parallel hinge arms 88 that extend therefrom. The thumb rotation plate 10 is affixed to the central region of the palmar plate 8 by alignment of its central opening 89 with the palmer plate's central orifice 86 below, both sandwiched between the wrist's top bracket 90. The wrist's top bracket 90 has an orifice that when aligned with the central opening 89 will accept the insertion of mechanical fastener 101 therethrough. In this manner the thumb rotation plate 10, the palmer plate 8 and the wrist top bracket 90 may all pivot relative to each other. This mechanical pinning with fastener 101 is similar to that used to lock the index digit 28 and the thumb digit assembly 6.

Between the parallel hinge arms 88 of the thumb rotation plate 10 is pivotally affixed the thumb pivot flange 12. This pivot flange 12 has a pair of parallel ears 95 that are substantially similar to the hinge arms 88. The ears 95 are located atop each of the hinge arms 88 and at least one thumb pivot pin 96 inserted therethrough. This may be accomplished in a fashion similar to that of the digit joints as outlined herein.

There is a torsion coil spring 102 around the thumb pivot pin 96 that functions to apply rotational torque between the thumb rotation plate 10 and the thumb pivot flange 12 so as to keep the thumb digit assembly 6 in an open position relative to the palmar plate 8. This ensures that as the user approaches an object to manipulate, the thumb is not initially in the way of the operation. This gives a maximally open position for grasping.

The wrist top bracket 90 (FIGS. 4 and 16) is matingly engaged for adjustable lockable pivotal positioning with the wrist bottom bracket 124. Again this uses a mechanical fastener 126 passing through a series of aligned orifices 128 in these wrist components similar to the system employed with the index digit. The bottom wrist bracket 124 may be affixed to the rest of the prosthesis in a plethora of ways commonly known in the field. It accommodates the passage of the cables 72 to their intended control points.

The mechanical hand as disclosed herein, has been discussed in association with uses as a prosthetic hand although use in the robotics industry is anticipated with a series of operable servo motors or other actuators controlling the various finger or thumb digits.

From the disclosure it can be seen that the present invention prosthetic hand has a plethora of capabilities not previously provided in the prior art prosthetic hands. The present invention incorporates a palm area which is both crushable and durable. The hand is load-bearing in both the palm area and fingers for maximum utility. At the same time, the movable metacarpal members are compliant to outside loads and passively wrap around irregularly shaped objects for better grasp. Movable metacarpals also result in the most realistic hand shake ever experienced, especially when compared to blocky palms of prior art. The crushable palm feature prevents damage to the hand, and provides a life-like springiness as a result of the overall connectivity and flexibility of the system as a whole. A passive thumb sling closes the thumb around handles or objects with no input required from the user, further contributing to the life-like performance. Optional fixation of the index digit assembly or thumb digit assembly provides further utility as needed, while maintaining crushability. The rotatable thumb digit assembly features adjustable opposable-angle positioning. The hand is both scalable and scalable proportionately because each of the segments of the digits, the palmar plate, the thumb pivot plate and the wrist are individually sizeable. Likewise, all components of the prosthetic hand distal of the wrist are similarly scalable. This allows for individual customization of geometric configurations tailored to specific use patterns (e.g. longer fingers wherever needed.) The prosthetic hand can be powered either by the body (manual) or by a motive source (electricity, hydraulics etc.) under myoelectric signal operation. The hand's palm is crushable since it is capable of having flexible and pivotable connections between rigid members along the length and width of the hand. It is waterproof having a lack of sensitive electronics. It has a strong lightweight design due to the hollow tubular member design. It is modular wherein individual parts can be replaced for quick repair. It can perform multiple tasks because of its individually adjustable, controllable finger digit assemblies. From an aesthetics point, it is visually pleasing and able to be offered in colors and with textured gripable soft resilient digit sleeves. The hand can be configured in either the voluntary-open or voluntary-closed position by simply installing the springs in the finger digit assemblies in a reverse manner. It will deform before failing, thereby giving indication of overload before failure, which is very important for an amputee with no biological feedback. Its body powered version will be "plug and play" into the existing prior art sockets allowing patients to have the option of switching out prosthetic hands and not having to relearn how to work their cable harness. In this way, every amputee currently using a body-powered hook will be able to swap out their hook for this body-powered flexible hand. It offers excellent visibility of objects grasped due to the open palm structure. Finally, the hollow digit structure allows ample room to add future internal components related to emerging technology, (e.g. tactile response, pressure sensors, heat sensors, etc.).

Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Having thus described the invention, what is claimed as new and desired to be secured by Letters Patent is as follows:

1. A mechanical hand comprising;

at least two finger digit assemblies each with a proximal end having a parallel pair of palm flanges that lie in a plane perpendicular to a plane in which said finger digit assemblies curl, said proximal ends of said finger digit assemblies defining part of a crushable palm of the mechanical hand;

a thumb digit assembly, said thumb digit assembly capable of opposable contact with at least one of said finger digit assemblies; and a support means for operationally supporting said finger digit assemblies and said thumb digit assembly for digital movement, wherein said thumb digit assembly and said pairs of palm flanges of said finger digit assemblies are connected to said support means by a pivotal connection that allows movement only in a lateral direction that is perpendicular to a direction of curl of the finger digit assemblies, so as to allow for a crushable movement of said crushable palm.

2. The mechanical hand of claim 1 wherein each of said finger digit assemblies is made from a hingeably connected, linear series of separately scalable elements; said finger digit assemblies capable of independent curling or straightening by action of at least one tensioned cable passing through said scalable elements.

3. The mechanical hand of claim 2 wherein said separately scalable elements are tube sections made of varying dimensions so as to allow scalability of said finger digit assemblies digits.

4. The mechanical hand of claim 3 wherein said separately scalable elements of each said finger digit assembly consecutively includes a distal phalange digit, a middle phalange digit, a proximal phalange digit and metacarpal digit; and wherein a linear series of tube sections of said thumb digit assembly consecutively includes a thumb distal phalange digit, a thumb proximal phalange digit and a thumb metacarpal digit.

5. The mechanical hand of claim 4 wherein said tube sections of said finger digit assemblies each have a longitudinal axis, a distal end and a proximal end, each end of said middle phalange digits and said proximal phalange digits includes a pair of parallel, generally planar coupling flanges with pivot pin orifices formed therethrough; each distal end of the metacarpal digits including a pair of parallel, generally planar coupling flanges with pivot pin orifices formed therethrough; each proximal end of the distal phalange digits including a pair of parallel, generally planar coupling flanges with pivot pin orifices formed therethrough wherein said coupling flanges of all adjacent tube sections within each linear series of tub sections reside aligned and connected with pivot pins for relative motion of said tube sections.

6. The mechanical hand of claim 5 wherein each linear series of tube sections has at least two cable guides thereon that guide at least one tensioned cable.

7. The mechanical hand of claim 6 wherein each said pair of coupling flanges on said distal phalange digits, said middle phalange digits, and said proximal phalange digits reside parallel to a same plane.

8. The mechanical hand of claim 7 wherein each on said metacarpal digit said pair of coupling flanges at said distal end are perpendicular to said pair of palm-flanges at said proximal end.

9. The mechanical hand of claim 8 wherein within each said linear series said pair of coupling flanges at said distal end of said metacarpal digit is hingedly connected to said coupling flanges at said proximal end of said proximal phalange digit and said coupling flanges at said distal end of said proximal phalange digit is hingedly connected to said coupling flanges at said proximal end of said middle phalange digit and said coupling flanges at said distal end of said middle phalange digit is hingedly connected to said coupling flanges at said proximal end of said distal phalange digit.

10. The mechanical hand of claim 9 further comprising:
a series of interchangeable strength, reversible springs placed around said pivot pins, each spring having spring legs extending 180 degrees apart from said spring and extending into said tube sections so as to generate a closing or opening sequence of said digits which may be altered by selection of differing strength springs.

11. The mechanical hand of claim 1 further comprising:
at least one flexible knuckle spacer;
wherein each said finger digit assembly is comprised of a linear assembly of individual finger digits with a metacarpal digit at said proximal end of said finger digit assembly;
wherein said at least one flexible knuckle spacer is operationally disposed between said metacarpal digits of adjacent said finger digit assemblies.

12. The mechanical hand of claim 11 further comprising a flexible thumb sling connected between the thumb digit assembly and an adjacent one of said finger digit assemblies.

13. The mechanical hand of claim 12 further comprising a compressible, flexible plain bearing between said support means and each said metacarpal digit.

14. The mechanical hand of claim 12 wherein said thumb digit assembly has a linear axis when said thumb digit assembly is fully extended, said thumb digit assembly being rotatable about said linear axis so as to enable adjustable angle opposable contact with at least one of said finger digit assemblies.

* * * * *